(12) United States Patent
Gardner et al.

(10) Patent No.: US 8,859,280 B2
(45) Date of Patent: Oct. 14, 2014

(54) CULTURE MEDIA FOR DEVELOPMENTAL CELLS CONTAINING ELEVATED CONCENTRATIONS OF LIPOIC ACID

(71) Applicant: Vitrolife Sweden AB, Kungsbacka (SE)

(72) Inventors: David K Gardner, Mckinnon (AU); Mark G Larman, Melbourne (AU); Donald Linck, Denver, CO (US)

(73) Assignee: Vitrolife Sweden AB, Göteborg (SE)

( * ) Notice: Subject to any disclaimer, the term of this patent is extended or adjusted under 35 U.S.C. 154(b) by 53 days.

(21) Appl. No.: 13/974,421

(22) Filed: Aug. 23, 2013

(65) Prior Publication Data

US 2013/0344595 A1    Dec. 26, 2013

Related U.S. Application Data

(62) Division of application No. 12/598,313, filed as application No. PCT/US2008/059897 on Apr. 10, 2008, now abandoned.

(60) Provisional application No. 60/915,180, filed on May 1, 2007.

(51) Int. Cl.
*C12N 5/02* (2006.01)
*C12N 5/073* (2010.01)

(52) U.S. Cl.
CPC .......... *C12N 5/0604* (2013.01); *C12N 2500/44* (2013.01)
USPC ............. 435/366; 435/383; 435/384; 800/24; 800/25

(58) Field of Classification Search
None
See application file for complete search history.

(56) References Cited

U.S. PATENT DOCUMENTS 5,972,923 A    10/1999    Simpkins et al.

FOREIGN PATENT DOCUMENTS

| WO | 98/08934 | 3/1998 |
|---|---|---|
| WO | 99/35242 | 7/1999 |
| WO | 2006/103300 | 10/2006 |

OTHER PUBLICATIONS

Steptoe, P.C. and Edwards, R.G., Lancet 2(8085): 366 (1978).
Pershadsingh HA, Expert Opin Investig Drugs 16:291-302 (2007).
Holmquist et al., Pharmacol Ther. 113: 154-64 (2007).
Kane et al., Biology of Reproduction, 39, 1137 (1988).
Kane, J. of Expt. Zoology, 245, 220 (1988).
Quinn, P., Harlow, G.M., "The effect of oxygen on the development of preimplantation mouse embryos in vitro", J. Exp. Zool., Oct. 1978, 206(1):73-80.
Thompson, JG., Simpson, A.C., Pugh, P.A., Donnelly, P.E., Tervit., H.R., "Effect of oxygen concentration on in-vitro development of preimplantation sheep and cattle embryos," J. Reprod. Fertil., Jul. 1990, 89(2):573-8.
Desai et al., Human Reprod 12: 328-335 (1997).
McKiernan SH and Bavister BD, Human Reprod 15: 157-164 (2000).
Dovinova et al., Neoplamsa, vol. 46, pp. 237-247 (1999).
Mizuno et al., Biochem. Biophys. Res. Commun., vol. 200, pp. 1134-1136 (1994).
International Search Report completed on Jul. 21, 2008, and mailed on Aug. 5, 2008.
Lockhart B. et al., "Inhibition of L-homocysteic acid and buthionine sulphoximine-mediated neurotoxicity in rat embryonic neuronal cultures with alpha-lipoic acid enantiomers." Brain Research vol. 855, No. 2, Feb. 2000, pp. 292-297.
David K. Gardner & Michelle Lane, Embryo Culture Systems, in Handbook of In Vitro Fertilization, Second Edition, pp. 205-264 (Alan O. Trounson & David K. Gardner eds., CRC Press LLC, 2000).

*Primary Examiner* — Jim Ketter
(74) *Attorney, Agent, or Firm* — Pearne & Gordon LLP (57) ABSTRACT

A composition and method for in vitro fertilization is provided which uses culture media comprising elevated concentrations of lipoic acid. More specifically, the invention provides culture media for developmental cells having a lipoic acid concentration of 5 μM to 40 μM. Culture media that include lipoic acid at concentrations within the identified range are able to provide blastocysts with increased survival, increased cell numbers, increased inner cell masses and/or increased percentage of the total mass made up by the inner cell compared to blastocysts cultured in a control medium.

11 Claims, 3 Drawing Sheets

FIG. 1

Embryos were cultured in 20% oxygen.
n = 200 embryos cultured per treatment.
**, significantly different from the controls.

FIG. 2

Embryos were cultured in 5% oxygen.
n = 200 embryos culture per treatment.
**, significantly different from the controls.

FIG. 3

CULTURE MEDIA FOR DEVELOPMENTAL CELLS CONTAINING ELEVATED CONCENTRATIONS OF LIPOIC ACID

CROSS-REFERENCE TO RELATED APPLICATIONS

This application is a divisional of U.S. application Ser. No. 12/598,313, which was the National Stage of International Application No. PCT/US2008/059897, filed Apr. 10, 2008, which claims the benefit of U.S. Provisional Application No. 60/915,180, filed May 1, 2007. Each of the above-listed applications are incorporated herein by reference.

FIELD OF THE INVENTION

The present invention relates generally to mammalian in vitro fertilization (IVF) and to culture media and processes useful for carrying out fertilization and embryo development and for carrying out stem cell growth. In particular, the invention provides a culture medium comprising an elevated concentration of lipoic acid that supports the growth and development of developmental cells, including embryos, and significantly increases the likelihood of successful pregnancy in IVF.

BACKGROUND OF THE INVENTION

The following description is provided to assist the understanding of the reader. None of the information provided or references cited is admitted to be prior art to the present invention.

In vitro fertilization is a technique used to overcome various forms of male and female infertility. The process involves fertilizing an oocyte with a sperm in vitro and subsequently transferring the developing embryo into the female body. Even though it has been nearly 30 years since the first birth from IVF (Steptoe, P. C. and Edwards, R. G., Lancet 2(8085): 366 (1978)), the process faces continuing challenges of low implantation and pregnancy rates. In the first ten years following the birth of the first "test tube baby," the reported success rate for IVF was only 8 to 10%. This low success rate was due, at least in part, to the poor quality of the embryo culture media. Unfortunately, despite a continuous effort to improve and specialize IVF culture media over the last 30 years, the success rate has only increased to approximately 30 to 35% in instances where single transfer is employed (based on national IVF registers in Finland and Sweden 2005). This single transfer data is the data most comparable to the 1978 data. This slow progress in improving IVF success rates reflects the difficulty and unpredictability in altering and enhancing culture media for developmental cells, such as gametes, zygotes and embryos.

The types of media presently used for human IVF have fallen into two categories; simple and complex. Simple media are those, such as Earle's and human tubal fluid (HTF), which are balanced salt solutions with added carbohydrate energy sources such as pyruvate, lactate and glucose. Complex media, such as Ham's F-10, further include non-essential and essential amino acids as well as other additives, such as vitamins, antibiotics and serum or proteins.

Although some IVF culture media are intended to support embryo development up to the 8-cell stage or beyond in a single medium, the trend has been to optimize separate culture media to support the developing embryo at different stages of development. This has led to the widespread use of sequential culture medium in IVF. For example, a sequential culture media system may use one culture medium for the growth of an embryo from a one-cell zygote to an eight-cell embryo during the first 48 hours of development and another culture medium to grow the eight-cell embryo to the blastocyst stage. As the female reproductive tract provides a changing environment for the developing embryo, the sequential culture media are designed to more closely mimic the female reproductive tract during in vivo embryo growth. The media compositions typically differ with respect to components such as amino acids and sugars to improve optimization of the media to support the embryonic growth and development.

The culture media employed in IVF have undergone some evolution over the course of the last 30 years. However, in some respects the culture media have remained strikingly unchanged. The focus of most of the research aimed at improving embryo culture media has been on the components that make up the core or bulk of the media—carbohydrate energy sources, amino acids, serum and salts/buffers. Other ingredients have received far less attention. In some cases it appears that these ingredients have been included in embryo culture media simply because they were present in the early somatic cell culture media from which embryo culture media initially evolved. Lipoic acid (LA) is one such ingredient.

Lipoic acid, also known as α-lipoic acid or thioctic acid, is widely known for its role as the coenzyme of the E2 (dihydrolipoate acyltransferase) subunit of multienzymatic complexes catalyzing oxidative decarboxylation of pyruvate, α-ketoglutarate, and branched-chain α-ketoacids. However, over the past ten years or so, it has become evident that lipoic acid is also an antioxidant. The efficiency of lipoic acid has been attributed to unique antioxidant properties of the lipoate/dihydrolipoate system, its reactive oxygen species (ROS) scavenging ability, and significant effect on the tissue concentrations of reduced forms of other antioxidants, including one of the most powerful, glutathione. Data from the literature suggests that lipoic acid and dihydrolipoate (DHLA) may or may not have growth promoting effects on specific cell types as murine leukemic cells and Jurkat T cells. Steptoe, P. C. and Edwards, R. G., Lancet 2(8085): 366 (1978).

Lipoic acid is a disulfide, amphiphilic compound which contains a chiral center creating two enantiomeric forms (R and L), with the most biologically active being the R-enantiomer. The disulfide component provides the molecule with metal-chelating properties while the compound's amphiphilic properties allow the relatively small molecule (MW=206.34 g/mol) to readily diffuse across the cell membrane where it is converted easily to its dithiol, reduced form, DHLA by several cellular multienzyme complexes involved in the decarboxylation of α-ketoacids; aerobically important steps in energy metabolism. Additionally, the DHLA/LA couple has a reported redox potential of −0.29 V making the pair a strong electron acceptor/oxygen radical scavenger unit. This strong redox potential allows the molecule to act as a potential recycler of other antioxidants such as vitamin C, vitamin E, glutathione, coenzyme Q10, and ubiquinone. Although the reduction of lipoic acid is presumed to take place within cells, the DHLA generated is thought to leak from the cells into the surrounding medium implicating both intracellular and extracellular antioxidant capabilities.

Lipoic acid is universally present in prokaryotes and eukaryotes. Lipoate, the unprotonated base, is the most prevalent form at physiological conditions and is thought to be synthesized within the cell by lipoic acid synthetase from the precursors' octanoic acid and a sulfur source, most likely a cysteine residue. This makes the molecule a non-essential nutrient, although it has been reported to be a valuable dietary supplement in diseases associated with excessive oxidative stress, including arthritis, diabetes, atherosclerosis, metabolic syndrome, and Alzheimer's. See, e.g., Pershadsingh H A, *Expert Opin Investig Drugs* 16:291-302 (2007); Holquist et al., *Pharmacol Ther.* 113: 154-64 (2007).

Despite the increasing body of knowledge regarding the role of lipoic acid in the body, very little is known about its effect on the growth of developmental cells, such as embryos, in culture. Although lipoic acid is sometimes included at low concentrations in embryo culture media, it is usually absent. The two studies that have systematically investigated the role of lipoic acid in embryo culture media concluded that the omission of lipoic acid from an embryo culture medium did not have an effect on outcome. The first study looked at the effect of 11 water-soluble vitamins, including lipoic acid, from Ham's F10 medium on the development of 8-cell hamster embryos to hatching and hatched blastocysts in vitro. (Kane et al., *Biology of Reproduction*, 39, 1137 (1988).) The study concluded that the omission of lipoic acid on the development of 8-cell hamster embryos resulted in no significant effect on the development at any stage of culture. The second study observed the effect of the omission of the 11 water-soluble vitamins, including lipoic acid, of Ham's F10 medium on the culture of rabbit morulae to expanded blastocysts. (Kane, *J. of Expt. Zoology*, 245, 220 (1988).) This study also concluded that there was no significant effect due to the omission of lipoic acid. Nonetheless, lipoic acid has been included in some embryo culture media.

For reasons that are not clear from the published literature, those embryo culture media that include lipoic acid limit the concentration to 1 µM or lower. This is likely due to the fact that many embryo culture media initially evolved from Ham's F10 and F12 media, early and still common somatic culture media, that happened to include lipoic acid at a concentration of 1 µM. However, it is clear from the studies cited above that the necessity or even desirability of including lipoic acid in such media was not a consideration during the early adoption of Ham's F10 and F12 media as the base for early embryo culture media. This is also clearly shown by the fact that none of the current major commercial embryo culture media products appear to contain any lipoic acid at all. In fact, the trend in the evolution of somatic cell culture media from Ham's F10 and F12 has also been toward dilution of those media, resulting in culture media with even lower concentrations of lipoic acid. For example, a popular culture medium that followed Ham's F12 is DMEM/F12 which is a 1+1 dilution of Ham's 12 with Dulbecco's modified Minimal Essential Medium (DMEM), another culture medium that is free of lipoic acid. RDF is another common culture medium that came later and built on DMEM/F12. RDF is a 1+1 dilution of DMEM/F12 with RPMI 1640, another culture medium that is free of lipoic acid. Thus, trends in the evolution of culture media from Ham's F10 and F12 demonstrate that the role of lipoic acid in culture media has been overlooked and unappreciated.

Lipoic acid has also been included in somatic cell culture media at other concentrations, however, the concentration of lipoic acid used in such media varies over many orders of magnitude and it has been acknowledged that "successful in vitro culture of different cell types will often require the use of different media formulations." (See, for example, PCT application publication number WO 98/08934.) This is particularly true for culture media for developmental cells, such as embryos, which have very different requirements from somatic cells. In addition, even within the somatic cell culture field, there is disagreement as to whether lipoic acid is beneficial in a culture medium. (See, for example, PCT application publication number WO 99/35242, page 44, stating "α-Lipoic acid (thioctic acid) is sometimes added to culture media, but there is little evidence that it is actually needed.") As such, the literature regarding the use of lipoic acid in somatic cell culture media sheds no light on the desirability or effect of lipoic acid in culture media for developmental cells, such as gametes, zygotes and embryos.

SUMMARY OF THE INVENTION

The present invention provides improved culture media for mammalian developmental cells, particularly embryos, and mammalian stem cells. The invention further provides methods for culturing mammalian developmental cells in the culture media. The culture media are characterized by a well-defined lipoic acid and/or or lipoic acid derivative concentration range that is at least 5 times, and more desirably at least 10 times, that of any other known embryo culture media. Culture media that include lipoic acid or lipoic acid derivatives at concentrations within the range identified by the inventors are able to provide blastocysts with increased survival, increased cell numbers, increased inner cell masses and/or increased percentage of the total mass made up by the inner cell relative to blastocysts cultured in a control medium. This is significant because these factors are recognized as predictors of embryo well being and successful future development into a fetus inside the uterus.

In one specific embodiment, the culture medium includes water, inorganic salts, at least one energy source, and lipoic acid at a concentration of 5 µM to 40 µM. In one embodiment, the medium further includes one or more amino acids. This includes culture media having lipoic acid concentrations of 5 µM to 20 µM, further includes culture media having lipoic acid concentrations of 5 µM to 15 µM, further includes culture media having lipoic acid concentrations of 8 µM to 12 µM and still further includes culture media having a lipoic acid concentrations of about 10 µM. The culture media may optionally include other ingredients, such as, but not limited to, growth factors, hormones, vitamins and antibiotics.

The culture media may be tailored to support the growth of developmental cells from a first developmental stage to a second developmental stage. For example, a culture medium may be designed to support a mammalian embryo up to the 4-cell stage, up to the 8-cell stage or up to the blastocyst stage. Thus, the various culture media encompassed by the present invention may include different components at varying concentrations.

Further objects, features and advantages of the invention will be apparent from the following detailed description when taken in conjunction with the accompanying drawings.

DETAILED DESCRIPTION

The present invention provides IVF and stem cell culture media compositions comprising elevated concentrations of lipoic acid and/or lipoic acid derivatives that support the development of gametes, zygotes and/or embryos in vitro prior to implantation. More specifically, the present IVF culture media comprise lipoic acid and/or lipoic acid derivatives at a concentration of 5 µM to 40 µM. Within this range, the maximum improvement to embryo development occurs at approximately 10 µM. Therefore, the culture media of the present invention also embrace media having a lipoic acid and/or lipoic acid derivative concentration within more defined ranges, including, for example, 5 µM to 20 µM, 5 µM to 15 µM and 8 µM to 12 µM, preferably about 10 µM. Thus, the present invention provides culture media for mammalian embryos which have at least a five-fold increase, and desirably at least a ten-fold increase, in lipoic acid concentration compared to known embryo culture media that include lipoic acid.

The culture media and uses thereof described herein have significant non-commercial and non-industrial uses (e.g., research) in addition to (or as an alternative to) commercial and industrial uses. This invention is not intended to support commercial uses of human embryos which are prohibited by law.

The term "culture medium" is used throughout the present specification to refer to aqueous media containing salts and carbohydrates prepared to a defined osmolarity and pH which is used for in vitro culture of developmental mammalian cells such as stem cells, gametes, zygotes and embryos. Such media can be prepared in the laboratory by any practitioner skilled in the art and are also commercially available. Although much of the discussion that follows focuses on culture media for developing embryos, it should be understood that the culture media may also be used to develop and culture stem cells, gametes and zygotes.

The term "embryo" is used to refer to cells in all stages of development from a fertilized egg up to the first 5 or 6 days.

The term "developmental cell" is used to refer to stem cells, gametes, zygotes and embryos.

The invention is based, at least in part, on the inventors' discovery that culture media comprising lipoic acid at a concentration in the range of 5 µM to 40 µM substantially improves the success rate of IVF procedures compared to culture media that omit lipoic acid, or that include lipoic acid at concentrations outside of this range. While not wishing or intending to be bound by theory, the inventors believe that the benefits provided by an elevated lipoic acid concentration in a culture medium for developmental cells results from the interplay of a variety of effects. The antioxidative effects of lipoic acid likely play an important role in the medium. Specifically, addition of lipoic acid to the culture is believed to play a role in protecting developing cells against oxidative damage caused by free radicals and reactive oxygen species. However, other effects also likely contribute to the benefits and help to define the narrow effective range for lipoic acid in a culture medium for gametes, zygotes and embryos. These effects include the possibility of an increase in the intercellular levels of GSH and chelating effects, in addition, the benefits due to increased levels of lipoic acid in a culture medium may be the result of various metabolic products of lipoic acid which exist at various stages of the metabolism of lipoic acid within the developmental cells. For example, the benefits may originate with derivatives of lipoic acid, such as methylated lipoic acid or DHLA.

The improvements provided by the present media may be measured by one or more of several parameters. These include increased survival rates for blastocysts up to the 4- or 5-day stage, blastocysts with a greater number of cells, blastocysts having larger inner cell masses and blastocyst having inner cell masses that make up a greater percent of the total. The present inventors have found that culture media having a lipoic acid concentration outside the range of 5 µM to 40 µM fail to provide these beneficial effects, and may even have a detrimental effect on embryo development. For example, the inventors have discovered that adding lipoic acid to cultures at less than 5 µM shows little, if any, effect on (i) the progression of embryos in culture to the blastocyst stage, (ii) the number of cells in the blastocysts in vitro, or (iii) the inner cell mass of the blastocysts. In contrast, embryos cultured in media comprising at least 5 µM lipoic acid exhibit all of these beneficial effects. Likewise, the beneficial effects of lipoic acid are lost when it is added to culture media at concentrations greater than about 40 µM. Above this concentration, there is a tendency for lower day 4 blastocyst development and decreased cell numbers. Thus, it appears that lipoic acid is only effective over a critical range.

The improvement in embryo development resulting from the use of the present culture media may be quantified by comparing embryos cultured in an improved medium containing high concentrations of lipoic acid and/or derivatives thereof (i.e., 5 µM to 40 µM) with embryos cultured in a control medium which differs from the improved medium only in that lipoic acid or derivatives thereof are absent from the control. For example, when fertilized mammalian zygotes (e.g., CF1 mouse zygotes) are cultured in the present medium up through day 4 or day 5, the present culture media may provide at least a 5%, at least a 10%, or even at least a 15% increase in one or more of the following: (1) percent compacting on day 3; (2) percent total blastocyst development on day 4; (3) percent total blastocyst development on day 5; and (4) percent blastocyst hatching on day 5. In addition, the present media may provide blastocysts with a total inner cell number and/or an increase in the percent of the total mass due to the inner cell which are at least 10% higher, or even at least 15% higher, than those of blastocysts cultured in the control medium.

The culture media of the present invention may be optimized to support embryo development at various stages. For example, the media may be optimized to culture an embryo up to the 4-cell stage, up to the 8-cell stage, from the 4-cell stage to the 8-cell stage, up to the blastocyst stage, or from the 4- or 8-cell stage to the blastocyst stage. Thus, the nature and concentration of the essential and non-essential ingredients of the cultures may vary, however, in each culture medium that includes lipoic acid (or a derivative thereof) the concentration of lipoic acid is desirably from 5 µM to 40 µM. In a sequential developmental cell culture, the lipoic acid or lipoic acid derivatives may be present in one media and absent in others.

The improvements offered by the present culture media may be achieved for blastocysts grown and developed under ambient oxygen conditions (e.g., about 20%) and reduced oxygen conditions (e.g., about 5%). This is important because most IVF programs culture gametes and embryos under ambient oxygen conditions, despite the fact that reduced oxygen conditions better simulate the environment of the uterus and provide better results. Quinn, P., Harlow, G. M., "The effect of oxygen on the development of preimplantation mouse embryos in vitro", *J. Exp. Zool.*, October 1978, 206 (1):73-80; Thompson, J. G., Simpson, A. C., Pugh, P. A., Donnelly, P. E., Tervit, H. R., "Effect of oxygen concentration on in-vitro development of preimplantation sheep and cattle embryos," *J. Reprod. Fertil.*, July 1990, 89(2):573-8. The reason for this is often the cost of a triple gas incubator required to culture under low oxygen conditions. The present media compositions therefore offer a culture medium better suited to accommodate embryos cultured under higher oxidative stress.

A typical culture medium for culturing developmental cells, such as embryos, will include water, inorganic salts, one or more energy sources, one or more amino acids (including non-essential and, optionally, essential amino acids), as core ingredients. Typical energy sources in an embryo culture medium include carbohydrate energy sources, such as pyruvate, lactate and glucose. Suitable inorganic salts include, $CaCl_2.2H_2O$, $CuSO_4.5H_2O$, $FeSO_4.7H_2O$, KCl, $MgSO_4$, NaCl, $NaHCO_3$, $Na_2HPO_4$, $ZnSO_4.7H_2O$, and $KHPO_4$. Non-essential amino acids include alanine, arginine, asparagine, aspartate, cysteine, glutamate, glutamine, glycine, proline, serine, and tryosine. Essential amino acids include histidine, isoleucine, leucine, lysine, methionine, phenylalanine, threonine, tryptophan, and valine. In addition to the lipoic acid and core ingredients the culture media will typically include other additives. These include vitamins, such as biotin, pantothenate, folic acid, niacinamide, pyridoxine, riboflavin, and thiamine, and further include growth factors, hormones and antibiotics, such as penicillin G and streptomycin sulfate. Albumin (e.g., human serum albumin or recombinant human albumin), polyvinylpyrolidone, hyaluronan, chelators, such as EDTA, and buffers, such as HEPES buffer or MOPS buffer, may also be added to the culture medium. Specific miscellaneous ingredients that also may be included in the culture media include, but are not limited to, choline chloride, hypoxanthine, inositol, thymidine, cyanocobalamine, cysteamine, phenol red and glutathione.

The concentration of the core ingredients and other additives in a culture medium may vary depending upon the stage of embryo development for which the medium is optimized. Typical concentrations for the inorganic salts in the culture media may be about 100 mM to about 150 mM or about 110 mM to about 140 mM. Typical concentrations for the energy sources in the media may be about 5 mM to about 40 mM, about 5 mM to about 30 mM, or about 5 mM to about 15 mM. Typical concentrations for the total amount of amino acids in the culture media may be about 0.1 mM to about 15 mM or about 0.5 mM to about 12 mM, or about 0.5 mM to about 6 mM. The amino acid composition and concentrations thereof may vary depending on the developmental stage of the cells in the culture media. The vitamins, growth factors, hormones and other miscellaneous ingredients in the culture medium tend to be added at fairly low concentrations, e.g., 1 mM or lower, 0.5 mM or lower, or even 0.1 mM or lower.

The present culture media may be formulated by adding enough lipoic acid or lipoic acid derivatives to existing embryo culture media to provide a lipoic acid or lipoic acid derivative concentration of 5 µM to 40 µM. Lipoic acid derivatives include molecules derived from lipoic acid that have equivalent or substantially equivalent biological effect with respect to improving the survival or development of developmental cells in culture. Thus, derivative of lipoic acid include, but are not limited to, methylated lipoic acid and DHLA. For the purpose of this application, derivatives also refers to other biologically active amphiphilic disulfide/thiotic molecules that have essentially equivalent physiological properties.

The lipoic acid or lipoic acid derivatives may be added as a mixture of enantiomeric forms, or as a single enantiomer. In the latter case, the R-enantiomer may be more desirable since it is more biologically active. For example, lipoic acid could be added to commercially-available simple culture media, such as human tubal fluid (HTF), Whittingham's T6 medium and Earle's balanced salt solution (EBSS) (available from Irvine Scientific) that have been supplemented with pyruvate, glucose and lactate as energy sources. These simple media have generally been employed in clinical IVF settings for oocyte insemination and cultivation of embryos until transfer on day 2 or 3. Lipoic acid may also be added to more complex embryo culture media designed to support early embryo growth. Such media include G1™ culture medium available from Vitrolife. This medium is designed to support the development of cleavage stage embryos to around the 8-cell stage. The medium contains carbohydrates, amino acids, and chelators to support the early embryo. The complete formulation for the G1 medium is provided in Table 1.

TABLE 1

Composition of G1 Culture Medium

| Component | A<br>Most Preferred<br>Concentration | B<br>Preferred<br>Range |
|---|---|---|
| NaCl | 90.08 | 80.0-100 |
| KCl | 5.5 | 3.5-7.5 |
| $NaH_2PO_4$ | 0.25 | 0.05-1.5 |
| $MgSO_4$ | 1 | 0.2-2.0 |
| $NaHCO_3$ | 25 | 15.0-30 |
| $CaCl_2$ | 1.8 | 0.8-2.8 |
| Glucose | 0.5 | 0.05-5.0 |
| NaLactate (L-isomer) | 10.5 | 5.0-20. |
| NaPyruvate | 0.32 | 0.1-1.0 |
| Alanine | 0.1 | 0.01-0.5 |
| Asparate | 0.1 | 0.01-0.5 |
| Asparagine | 0.1 | 0.01-0.5 |
| Glutamate | 0.1 | 0.01-0.5 |
| Alanyl - Glutamine | 0.5 | 0.1-1.0 |
| Glycine | 0.1 | 0.01-0.5 |
| Proline | 0.1 | 0.01-0.5 |
| Serine | 0.1 | 0.01-0.5 |
| Taurine | 0.1 | 0.01-10.0 |
| EDTA | 0.01 | 0.005-0.20 |
| HSA | 5 mg/ml | 1-10.0 mg/ml |
| Hyaluronate | 0.1 mg/ml | 0.02-0.5 mg/ml |

(The concentrations in Table 1 are provided in mM, unless otherwise indicated.)

Alternatively, lipoic acid or lipoic acid derivatives may be added to commercially available IVF culture medium capable of supporting embryos to beyond day 3 (8-cell stage). These culture media have been designed to carry embryos to the blastocyst stage prior to implantation. In accordance with the present invention, lipoic acid may be added to these media to enhance the blastocyst development even further. One example includes α-modified essential medium (αMEM), described in Desai et al., *Human Reprod* 12: 328-335 (1997). A second example includes HECM-6 medium plus pantothenate. McKiernan S H and Bavister B D, *Human Reprod* 15: 157-164 (2000). Other examples include the G2 media available from Vitrolife. G2 is a medium that is designed to support the development of the embryo from around the 8-cell stage (day 3) to the blastocyst stage. The medium (Table 2) contains carbohydrates, amino acids, and vitamins to support the later stage embryo.

TABLE 2

Composition of G2 Culture Medium

| Component | A<br>Most Preferred<br>Concentration | B<br>Preferred<br>Range |
|---|---|---|
| NaCl | 90.08 | 80.0-100 |
| KCl | 5.5 | 3.5-7.5 |
| $NaH_2PO_4$ | 0.25 | 0.05-1.5 |
| $MgSO_4$ | 1 | 0.2-4.0 |
| $NaHCO_3$ | 25 | 15-30.0 |
| $CaCl_2$ | 1.8 | 0.8-2.8 |
| Glucose | 3.15 | 0.5-5.5 |

TABLE 2-continued

Composition of G2 Culture Medium

| Component | A<br>Most Preferred<br>Concentration | B<br>Preferred<br>Range |
|---|---|---|
| NaLactate (L-isomer) | 5.87 | 2.0-20.0 |
| NaPyruvate | 0.1 | 0.01-1.0 |
| Alanine | 0.1 | 0.01-0.5 |
| Asparate | 0.1 | 0.01-0.5 |
| Asparagine | 0.1 | 0.01-0.5 |
| Glutamate | 0.1 | 0.01-0.5 |
| Alanyl - Glutamine | 1 | 0.01-2.0 |
| Glycine | 0.1 | 0.01-0.5 |
| Proline | 0.1 | 0.01-0.5 |
| Serine | 0.1 | 0.01-0.5 |
| L-Arginine-HCl | 0.6 | 0.1-1.2 |
| L-Cystine 2HCl | 0.1 | 0.05-0.25 |
| L-Histidine-HCl—H2O | 0.2 | 0.1-0.4 |
| L-Isoleucine | 0.4 | 0.1-0.8 |
| L-Leucine | 0.4 | 0.1-0.8 |
| L-Lysine-HC1 | 0.4 | 0.1-0.8 |
| L-Methionine | 0.1 | 0.05-0.25 |
| L-Phenylalanine | 0.2 | 0.1-0.4 |
| L-Threonine | 0.4 | 0.1-0.8 |
| L-Tryptophan | 0.5 | 0.1-0.9 |
| L-Tyrosine 2Na | 0.2 | 0.1-0.4 |
| L-Valine | 0.4 | 0.1-0.8 |
| D-Ca Pantothenate | 0.002 | 0.001-0.004 |
| Choline Chloride | 0.007 | 0.003-0.01 |
| Folic Acid | 0.0023 | 0.001-0.0045 |
| i-Inositol | 0.0111 | 0.005-0.02 |
| Niacinamide | 0.0082 | 0.004-0.016 |
| Pyridoxal HCl | 0.0049 | 0.002-0.01 |
| Riboflavin | 0.0003 | 0.0001-0.0006 |
| Thiamine HCl | 0.003 | 0.001-0.006 |
| HSA | 5 mg/ml | 1-10 mg/ml |
| Hyaluronate | 0.1 mg/ml | 0.02-0.5 mg/ml |

(The concentrations in Table 2 are provided in mM, unless otherwise indicated.)

In one embodiment, 8-cell stage embryos are transferred from an embryo culture medium optimized to support early stage growth (i.e., up to the 8-cell stage) supplemented with lipoic acid to an embryo culture medium optimized to support later stage growth (i.e., up to the blastocyst stage) Lipoic acid may or may not be added to the latter media.

The present culture media also may be formulated by adding enough lipoic acid or lipoic acid derivatives to existing gamete (oocyte or sperm) culture or freezing media to provide a lipoic acid concentration of 5 μM to 40 μM. Tables 3-5 below provide gamete culture media in which lipoic acid may be included to provide for improved cellular development and survival.

TABLE 3

Composition of Oocyte Maturation Medium

| Component | A<br>Most Preferred<br>Concentration | B<br>Preferred<br>Range |
|---|---|---|
| NaCl | 90.08 | 80.0-100 |
| KCl | 5.5 | 3.5-7.5 |
| NaH$_2$PO$_4$ | 0.25 | 0.05-1.5 |
| MgSO$_4$ | 2 | 0.2-4.0 |
| NaHCO$_3$ | 25 | 15-30.0 |
| CaCl$_2$ | 1 | 0.8-2.8 |
| Glucose | 3.15 | 0.5-5.5 |
| NaLactate (L-isomer) | 5.87 | 2.0-20.0 |
| NaPyruvate | 0.1 | 0.01-1.0 |
| Alanine | 0.1 | 0.01-0.5 |
| Asparate | 0.1 | 0.01-0.5 |
| Asparagine | 0.1 | 0.01-0.5 |
| Glutamate | 0.1 | 0.01-0.5 |

TABLE 3-continued

Composition of Oocyte Maturation Medium

| Component | A<br>Most Preferred<br>Concentration | B<br>Preferred<br>Range |
|---|---|---|
| Alanyl - Glutamine | 1 | 0.01-2.0 |
| Glycine | 0.1 | 0.01-0.5 |
| Proline | 0.1 | 0.01-0.5 |
| Serine | 0.1 | 0.01-0.5 |
| Cysteamine | 0.5 | 0.1-2.0 |
| L-Arginine-HCl | 0.6 | 0.1-1.2 |
| L-Cystine 2HCl | 0.1 | 0.05-0.25 |
| L-Histidine-HCl—H2O | 0.2 | 0.1-0.4 |
| L-Isoleucine | 0.4 | 0.1-0.8 |
| L-Leucine | 0.4 | 0.1-0.8 |
| L-Lysine-HCl | 0.4 | 0.1-0.8 |
| L-Methionine | 0.1 | 0.05-0.25 |
| L-Phenylalanine | 0.2 | 0.1-0.4 |
| L-Threonine | 0.4 | 0.1-0.8 |
| L-Tryptophan | 0.5 | 0.1-0.9 |
| L-Tyrosine 2Na | 0.2 | 0.1-0.4 |
| L-Valine | 0.4 | 0.1-0.8 |
| D-Ca Pantothenate | 0.002 | 0.001-0.004 |
| Choline Chloride | 0.007 | 0.003-0.01 |
| Folic Acid | 0.0023 | 0.001-0.0045 |
| i-Inositol | 0.0111 | 0.005-0.02 |
| Niacinamide | 0.0082 | 0.004-0.016 |
| Pyridoxal HCl | 0.0049 | 0.002-0.01 |
| Riboflavin | 0.0003 | 0.0001-0.0006 |
| Thiamine HCl | 0.003 | 0.001-0.006 |
| HSA | 5 mg/ml | 1-10.0 mg/ml |
| Hyaluronate | 0.25 mg/ml | 0.05-0.5 mg/ml |
| ITS | 10 ng/ml | 1-100 ng/ml |
| IGF-I | 100 ng/ml | 10-1000 ng/ml |
| EGF | 100 ng/ml | 10-1000 ng/ml |
| FSH | 0.1 U/ml | 0.01-10 U/ml |
| hCG | 0.1 U/ml | 0.01-10 U/ml |

*Concentrations are in mM, unless otherwise indicated; the medium is aqueous.

TABLE 4

Composition of Sperm Preparation and Fertilization Medium*

| Component | A<br>Most Preferred<br>Concentration | B<br>Preferred<br>Range |
|---|---|---|
| NaCl | 100 | 75-100 |
| KCl | 5.5 | 3.5-7.5 |
| NaH$_2$PO$_4$ | 0.5 | 0.05-1.5 |
| MgSO$_4$ | 1 | 0.2-4.0 |
| Glucose | 3.15 | 0.5-5.6 |
| NaLactate (L-isomer) | 5 | 2.0-20 |
| NaPyruvate | 0.32 | 0.1-0.5 |
| NaHCO$_3$ | 25 | 15-30 |
| CaCl$_2$ | 1.8 | 0.8-2.8 |
| Glutathione | 1 mg/ml | 0.5-5.0 mg/ml |
| Alanine | 0.1 | 0.01-0.5 |
| Asparate | 0.1 | 0.01-0.5 |
| Asparagine | 0.1 | 0.01-0.5 |
| Glutamate | 0.1 | 0.01-0.5 |
| Glycine | 0.1 | 0.01-0.5 |
| Proline | 0.1 | 0.01-0.5 |
| Serine | 0.1 | 0.01-0.5 |
| Taurine | 0.1 | 0.01-10.0 |
| HSA | 5 mg/ml | 1.0-10.0 mg/ml |
| Hyaluronate | 0.1 mg/ml | 0.02-0.5 mg/ml |
| Penicillin | 0.06 mg/ml | 0.01-0.1 mg/ml |
| Streptomycin | 0.05 mg/ml | 0.01-0.1 mg/ml |

*Concentrations are in mM unless otherwise indicated; the medium is aqueous.

TABLE 5

Composition of Medium for Intracytoplasmic Sperm Injection *

| Component | A<br>Most Preferred<br>Concentration | B<br>Preferred<br>Range |
|---|---|---|
| NaCl | 90.08 | 75.0-105 |
| KCl | 5.5 | 3.5-7.5 |
| $MgSO_4$ | 2 | 0.4-4 |
| $NaHCO_3$ | 5 | 2.0-10 |
| MOPS/HEPES | 20 | 10-25.0 |
| $CaCl_2$ | 1 | 0.5-2.0 |
| NaLactate (L-isomer) | 10.5 | 5.0-20 |
| NaPyruvate | 0.32 | 0.1-1.0 |
| Alanyl - Glutamine | 0.5 | 0.1-2.0 |
| Glycine | 0.5 | 0.1-2.0 |
| Proline | 0.1 | 0.05-2.0 |
| Serine | 0.1 | 0.05-2.0 |
| Taurine | 0.1 | 0.05-5.0 |
| HSA | 5 mg/ml | 1-10.0 mg/ml |
| Hyaluronate | 0.1 mg/ml | 0.02-0.5 mg/ml |
| PVP | 10% | 1-20% |

* Concentrations are in mM unless otherwise indicated; the medium is aqueous.

EXAMPLES

Example 1

Lipoic Acid Increases Blastocyst Cell Number of Cultured Embryos in accordance with the present invention, a culture media composition comprising lipoic acid was used during the development of mouse embryos in vitro. Lipoic acid at a concentration of 5 μM to 40 μM is shown to have significant beneficial effects on mouse embryo development, including a significant increase in blastocyst cell number and cell mass.

The following procedure was carried out. Lipoic acid was dissolved in ethanol. A 100 mM working solution in 100% EtOH was prepared with appropriate dilutions made to the culture media thereafter (1 μM, 10 μM and 100 μM final concentrations). A vehicle control, equivalent to the dilution of the highest concentration solution (0.1%), was used in all culture experiments. Zygotes were collected from 4-week-old CF1 outbred female mice. Cumulus-enclosed zygotes were collected at 21 h post hCG and denuded with 1 mg/mL hyaluronidase in G-MOPS supplemented with 5 mg/mL human serum albumin. Cultures were incubated at either 5% or 20% $O_2$. After four days of culture, blastocyst development was analyzed and cell number was counted in 200 cultured embryos per treatment.

Figure 1:
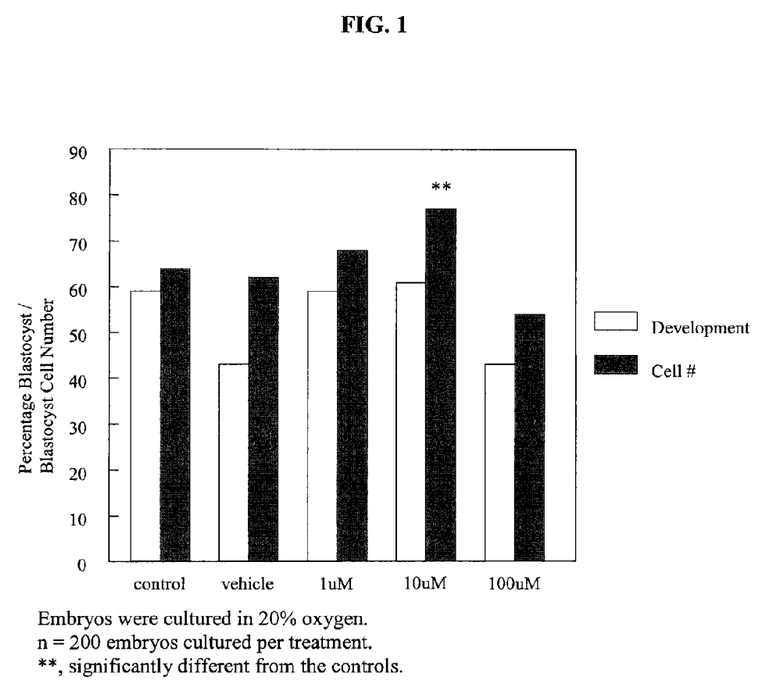
FIG. 1 presents data showing blastocyst development of mouse embryos in vitro at 20% $O_2$ in accordance with the present invention.
Figure 2:
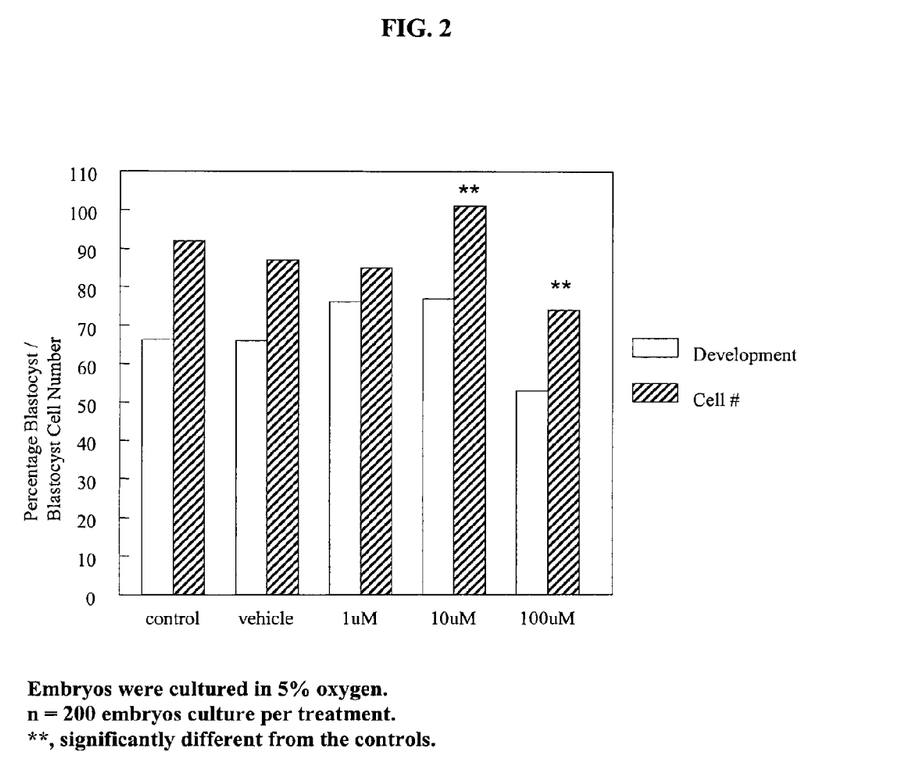
FIG. 2 presents data showing blastocyst development of mouse embryos in vitro at 5% $O_2$ in accordance with the present invention.

The results are shown in FIGS. 1 (20% $O_2$) and 2 (5% $O_2$). The data are based on 200 embryos cultured per study. When lipoic acid was tested over a concentration of 1 to 100 μM on outbred (CF1) mouse embryos in culture, resultant blastocysts had a significantly higher cell number when exposed to 10 μM. At a concentration of 1 μM lipoic acid, no statistically significant increase in cell number was observed at either 5% or 20% oxygen concentration. Furthermore, the beneficial effect of lipoic acid was lost at higher concentrations. In fact, at a concentration of 100 μM lipoic acid the embryos had significantly lower cell numbers than the corresponding embryos grown in the control medium. The data for FIGS. 1 and 2 are presented in Tables 6 and 7, respectively, which also provide the results for the trophectoderm, inner cell mass (ICM) and ICM ratio.

TABLE 6

| | n | Day 5<br>% Blast | trophectoderm | total cell # | ICM | ICM ratio |
|---|---|---|---|---|---|---|
| control | 202 | 58.91% | 51.17 | 64.49 | 13.28 | 20.60% |
| vehicle | 216 | 42.59% | 50.51 | 62.11 | 11.60 | 18.68% |
| 1 μM | 198 | 59.18% | 55.30 | 68.37 | 13.07 | 19.12% |
| 10 μM | 231 | 61.47%[‡] | 61.054[‡‡] | 77.527[‡‡‡] | 16.4731[‡‡‡‡] | 21.25% |
| 100 μM | 201 | 42.57% | 43.6667 | 53.9583 | 10.2916 | 19.07% |

[‡] $p < 0.0001$;
[‡‡] $p < 0.0022$;
[‡‡‡] $p < 0.0002$;
[‡‡‡‡] $p < 0.0001$, as calculated using Student's t-test

TABLE 7

| | | Day 5<br>% Blast | trophectoderm | total cell # | ICM | ICM ratio |
|---|---|---|---|---|---|---|
| control | n = 205 | 66.34% | 71.91 | 92.12 | 20.21 | 21.93% |
| vehicle | n = 209 | 66.03% | 69.99 | 87.81 | 17.82 | 20.29% |
| 1 μM | n = 209 | 76.15% | 68.57 | 85.40 | 16.83 | 19.71% |
| 10 μM | n = 215 | 76.74%[#] | 79.28[##] | 101.77[###] | 22.49[####] | 22.10% |
| 100 μM | n = 196 | 53.13% | 60.61 | 74.21 | 13.61 | 18.33% |

[#] $p < 0.023$;
[##] $p < 0.013$;
[###] $p < 0.002$;
[####] $p < 0.001$, as calculated using Student's t-test

Example 2

Lipoic Acid in Sequential IVF Cultures of Day 4 Mouse Embryos

CF1 mouse embryos were grown in either G1 alone or G1 plus 10 μM lipoic acid. After 48 hours, embryos from both treatment groups were moved to G2. All cultures were incubated in low $O_2$. Compaction rates were assessed and blastocyst developmental rates were measured at 71 and 78 hours. Blastocysts were then differentially stained and counted. The results are shown in Table 8. Addition of lipoic acid to G1 increased inner cell mass number and percentage inner cell mass of total.

TABLE 8

| Treatment | n | Day 3 % a.m. | Day 4 blast % a.m. | Day 4 blast % p.m. | % Expanded on Day 4 | TE | ICM | Total | % ICM |
|---|---|---|---|---|---|---|---|---|---|
| G1 (Control) | 58 | 81.0 | 22.7 | 51.7 | 19.0 | 34 ± 2 | 11.4 ± 1 | 45 ± 2 | 25% |
| G1 + 10 μM LA | 58 | 81.0 | 22.4 | 65.5 | 39.7 | 34 ± 2 | 16 ± 1** | 50 ± 2** | 31%** |

Significantly different from control;
*$P < 0.05$;
**$P < 0.01$, as calculated by Student's t-test

Example 3

Effective Concentration Range for Lipoic Acid on Mouse Embryo Development

The effective range of lipoic acid concentrations to enhance blastocyst development and cell number was established using CF1 mouse embryos. The results are shown in Table 9. The data show that lipoic acid is effective between 5 to 40 μM in promoting blastocyst development and increasing cell number. Above these concentrations, lipoic acid produces lower blastocyst development by day 5 and lower cell number relative to the control.

TABLE 9

Effect of Lipoic acid concentration on CF1 mouse zygote development cultured at 20% oxygen

| | n | Day 3 (% compacting) | Day 4 (% Total Blast) | Day 5 (% Total Blast) | Day 5 (% Hatching) | Total Cell Number |
|---|---|---|---|---|---|---|
| control | 66 | 34.3% | 50.0% | 75.0% | 34.4% | 80.2 ± 4.9 |
| 5 μM LA | 62 | 38.9% | 51.6% | 81.8% | 40.9% | 90.2 ± 4.8 |
| 10 μM LA | 62 | 51.4% | 62.9% | 92.7% | 40.0% | 91.3 ± 4.7 |
| 20 μM LA | 63 | 26.5% | 42.9% | 73.1% | 31.3% | 94.0 ± 7.2 |
| 40 μM LA | 67 | 22.9% | 37.3% | 74.6% | 28.4% | 69.4 ± 5.8 |
| 80 μM LA | 65 | 22.9% | 4.6% | 29.7% | 9.4% | 34.0 |

Example 4

Protective Effects of Lipoic Acid Against Reactive Oxygen Species

In order to determine whether the lipoic acid is having an antioxidant effect, a series of experiments were performed using the fluorescent dye 2',7'-dichlorodihydrofluorescein diacetate (H2DFFDA), which reacts with reactive oxygen species (ROS) intermediates. 200 μM H2DFFDA in DMSO was added to GMOPS-Plus (available from Vitrolife). Lipoic acid dissolved in EtOH with the final concentration within the media being 0.1% EtOH. Each drop was then photo-oxidized with 4 successive 2.5 minute exposures using UV light to generate ROS.

Figure 3:
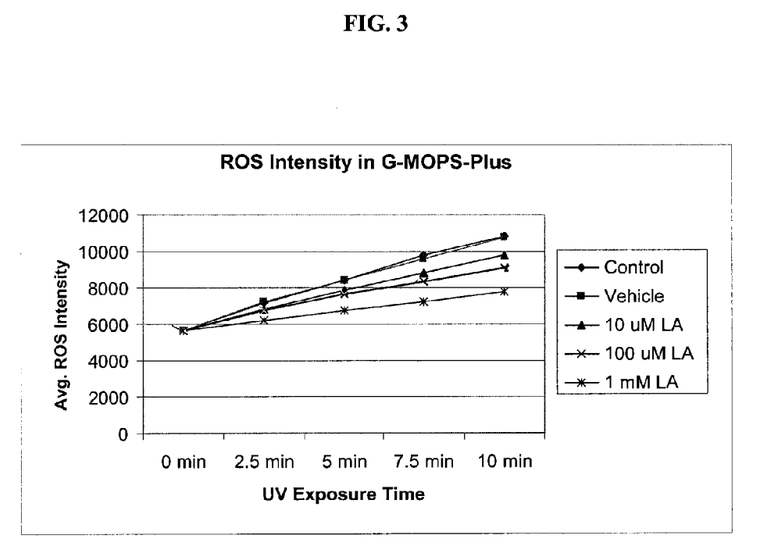
FIG. 3 presents data showing the inhibition of reactive oxygen species (ROS) in the presence of lipoic acid.

FIG. 3 shows the effects of lipoic acid in reducing the generation of ROS within the culture media. All results are based on comparison to the vehicle group (0.95% EtOH), which was not significant in comparison to the control group. The inclusion of lipoic acid at all concentrations resulted in a concentration-dependent decrease in the generation of reactive oxygen, thus indicating that lipoic acid is having an antioxidant effect.

Example 5

Effect of Lipoic Acid G-Media on Human Embryo Development

In accordance with the present invention, the effect of lipoic acid-containing culture media on human embryo development is examined. Good prognosis patients have half of their embryos cultured in G1 culture media free of lipoic acid (i.e., the control), while the other half are cultured in G1 medium containing 10 μM lipoic acid (i.e., the elevated lipoic acid medium).

The data are consistent with that obtained in the mouse model. Embryos develop quicker up to the 8-cell and blastocyst stage in the elevated lipoic acid medium compared to the control.

For the purposes of this disclosure and unless otherwise specified, "a" or "an" means "one or more". All patents, applications, references and publications cited herein are incorporated by reference in their entirety to the same extent as if they were individually incorporated by reference.

While the principles of this invention have been described in connection with specific embodiments, it should be understood clearly that these descriptions are made only by way of example and are not intended to limit the scope of the invention.

What is claimed is:

1. A method for culturing developmental cells, the method comprising culturing a stem cell, gamete, zygote or embryo in a developmental cell culture medium, wherein the culture medium comprises:
   (a) water;
   (b) inorganic salts;
   (c) at least one energy source; and
   (d) lipoic acid, lipoic acid derivatives or a combination thereof at a concentration of about 5 µM to about 40 µM.

2. The method of claim 1, wherein the culture medium further comprises one or more amino acids.

3. The method of claim 2, wherein the concentration of inorganic salts in the culture medium is about 115 mM to about 140 mM, the concentration of energy sources in the culture medium is about 5 mM to about 30 mM, and the total concentration of amino acids in the culture medium is about 0.1 to 15 mM.

4. The method of claim 1, wherein the culture medium further comprises a chelating agent, an antibiotic and hyaluronan.

5. The method of claim 1, wherein the culture medium supports the development of at least one of stem cells, gametes, zygotes or embryos from one developmental stage to another developmental stage.

6. The method of claim 1, wherein the stem cell, gamete, zygote or embryo is cultured under ambient oxygen conditions.

7. The method of claim 1, wherein the stem cell, gamete, zygote or embryo is cultured under reduced oxygen conditions.

8. The method of claim 1, wherein the step of culturing a stem cell, gamete, zygote, or embryo comprises culturing a human embryo.

9. The method of claim 1, wherein the step of culturing a stem cell, gamete, zygote or embryo comprises culturing an embryo up to the 8-cell stage.

10. The method of claim 1, wherein the step of culturing a stem cell, gamete, zygote or embryo comprises culturing an embryo up to the blastocyst stage.

11. The method of claim 1, wherein the step of culturing a stem cell, gamete, zygote or embryo comprises culturing an embryo from the 8-cell stage to the blastocyst stage.

* * * * *